United States Patent [19]

Cragoe, Jr. et al.

[11] 4,087,435
[45] May 2, 1978

[54] 8-AZA-9-DIOXOTHIAPROSTANOIC ACIDS

[75] Inventors: Edward J. Cragoe, Jr., Lansdale; James H. Jones, Blue Bell; John B. Bicking, Lansdale, all of Pa.

[73] Assignee: Merck & Co., Inc., Rahway, N.J.

[21] Appl. No.: 769,477

[22] Filed: Feb. 17, 1977

[51] Int. Cl.² ............................................. C07D 275/02
[52] U.S. Cl. ............................... 260/301; 260/293.68; 260/299; 260/455 R; 260/556 A; 424/270; 544/109; 544/367; 560/254; 560/238
[58] Field of Search .......................................... 260/301

[56] References Cited
U.S. PATENT DOCUMENTS 4,022,794  5/1977  Smith et al. ........................... 260/301

OTHER PUBLICATIONS

Ambrus et al., *Prostaglandins*, vol. 10, pp. 661–666 (Oct., 1975).

*Primary Examiner*—R. J. Gallagher
*Attorney, Agent, or Firm*—Thomas E. Arther; Harry E. Westlake, Jr.; Rudolph J. Anderson, Jr.

[57] ABSTRACT

Novel 8-aza-9-dioxothiaprostanoic acid compounds, their salts, and derivatives, are prepared from ethyl 7-(3-hydroxymethyl-2-isothiazolidinyl)-5-heptynoate S,S-dioxide by first hydrogenating the triple bond over a Lindlar catalyst, followed by mild oxidation, to produce the corresponding 3-formyl compound, which is condensed with the ylide prepared from dimethyl-(2-oxoheptyl)phosphonate to produce the $\alpha,\beta$-unsaturated ketone, followed by reduction to the corresponding carbinol, and ester hydrolysis. The compounds are useful especially for the treatment of patients with poorly functioning kidneys, as hypotensives, or as platelet aggregation inhibitors.

7 Claims, No Drawings

8-AZA-9-DIOXOTHIAPROSTANOIC ACIDS

SUMMARY OF THE INVENTION

This invention relates to novel 8-aza-9-dioxothiaprostanoic acid compounds, salts, and derivatives thereof which are represented by the formula:

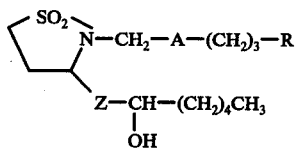

wherein R is selected from the group consisting of carboxy and a carboxy salt which incorporates a pharmaceutically acceptable cation, such as metal cations derived from alkali metals, alkaline earth metals, and amines such as ammonia, primary and secondary amines, and quaternary ammonium hydroxides. Especially preferred metal cations are those derived from alkali metals, e.g., sodium, potassium, lithium, and the like, and alkaline earth metals, e.g., calcium, magnesium, and the like, and other metals, i.e., aluminum, iron, and zinc.

Pharmaceutically acceptable cations can be formed from primary, secondary, or tertiary amines, or quaternary ammonium hydroxides such as methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, benzyltrimethylammonium, and the like.

R is also selected from alkoxycarbonyl (COOR$^1$) wherein R$^1$ is alkyl having 1–10 carbon atoms.

A is selected from the group consisting of ethylene and cis-vinylene.

Z is selected from the group consisting of ethylene and trans-vinylene.

BACKGROUND OF THE INVENTION

The prostaglandins are a biologically important class of naturally occurring acids that are derived, in a formal sense, by functionalization of the fundamental alicyclic C$_{20}$ fatty acid, prostanoic acid.

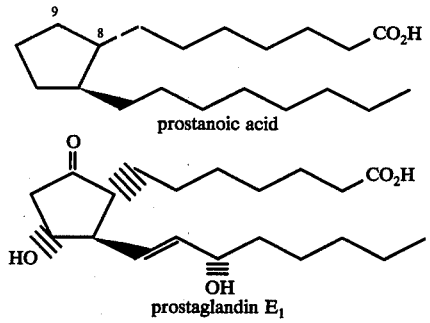

The naturally occurring prostaglandins are known to have a broad spectrum of biological activity. In particular, the E-series prostaglandins number among their useful actions hypotensive, renal vasodilatory, gastric antisecretory, bronchodilatory, and platelet aggregation inhibitory activities.

There is much evidence to show that the E prostaglandins express these activities by elevating the levels of cyclic adenosine monophosphate (CAMP) in the target cells. The compounds of this invention mimic the E prostaglandins in biological activity since they likewise markedly stimulate the formation of CAMP. For example, a compound of formula I, 7-[3-(3-hydroxy-1-trans-octenyl)-2-isothiazolidinyl]-5-cis-heptenoic acid S,S-dioxide, causes a 14-fold increase in CAMP compared to control in the mouse ovary at a concentration of 25 micrograms per milliliter.

The compounds of this invention are thus applicable to therapy particularly as (1) renal vasodilators for the treatment of patients with renal impairment, (2) hypotensives for the normalization of high blood pressure, and (3) platelet aggregation inhibitors useful in preventing the formation of thrombi.

Further, a major disadvantage of the prostaglandins has been overcome by the compounds of this invention. The prostaglandins are so rapidly metabolized and deactivated in bodily tissues that their actions are hardly seen except on intravenous administration. Adequate blood levels cannot be attained when the prostaglandins are administered orally. The compounds of this invention are not substrates for the principal prostaglandin degrading enzyme. They are thus only slowly metabolized, have adequate durations of action, and are biologically active when administered orally.

The compounds of this invention can be administered either topically or systemically, i.e., intravenously, subcutaneously, intramuscularly, orally, rectally, or by aerosolization in the form of sterile implants for long action. They can be formulated in any of a number of pharmaceutical compositions and non-toxic carriers to this end.

The pharmaceutical compositions can be sterile, injectable suspensions or solutions, or solid orally-administrable, pharmaceutically acceptable tablets or capsules; the compositions can also be intended for sublingual administration, or for suppository use. It is especially advantageous to formulate compositions in dosage unit forms for ease and economy of administration and uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile injectable composition can be aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative; for example, methylparaben, propylparaben, phenyl, and chlorobutanol. The aqueous vehicle can also contain sodium chloride, preferably in an amount to be isotonic; as well as a suspending agent, for example, gum arabic, polyvinyl pyrrolidone, methyl cellulose, acetylated monoglyceride (available commercially as Myvacet from Distillation Products Industry, a division of Eastman Kodak Company), monomethyl glyceride, dimethyl glyceride, or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol, and glucose. Additionally, the pH of the composition is adjusted by use of an aqueous solution such as tris(hydroxymethyl)aminomethane (tris buffer).

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2-50 mg./ml. Lower concentrations require needless quantities of liquid. Higher concentrations than 50 mg./ml. are difficult to maintain and are preferably avoided.

Oral administration forms of the drug can also be prepared for laboratory animals or human patients. The same dosage levels can be used as for injectable forms; however, even higher levels can be used to compensate for biodegradation in the transport. Generally, a solid unit dosage form can be prepared containing from 0.5 mg. to 25 mg. active ingredient.

Whatever the mode of administration, doses in the range of about 0.10 to 20 milligrams per kilogram of body weight administered one to four times per day are used, the exact dose depending on the age, weight, and condition of the patient and the frequency and route of administration.

CHEMICAL DESCRIPTION OF THE INVENTION

The carboxylic acids of the invention which are represented by formula II:

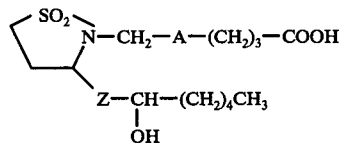

are prepared from a common intermediate, ethyl 7-(3-hydroxymethyl-2-isothiazolidinyl)-5-heptynoate S,S-dioxide (III), the method of synthesis of which is outlined in Scheme A:

Scheme A

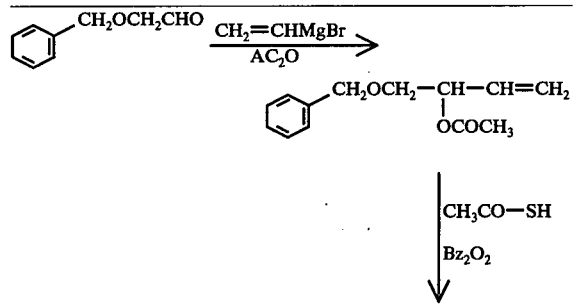

-continued
Scheme A

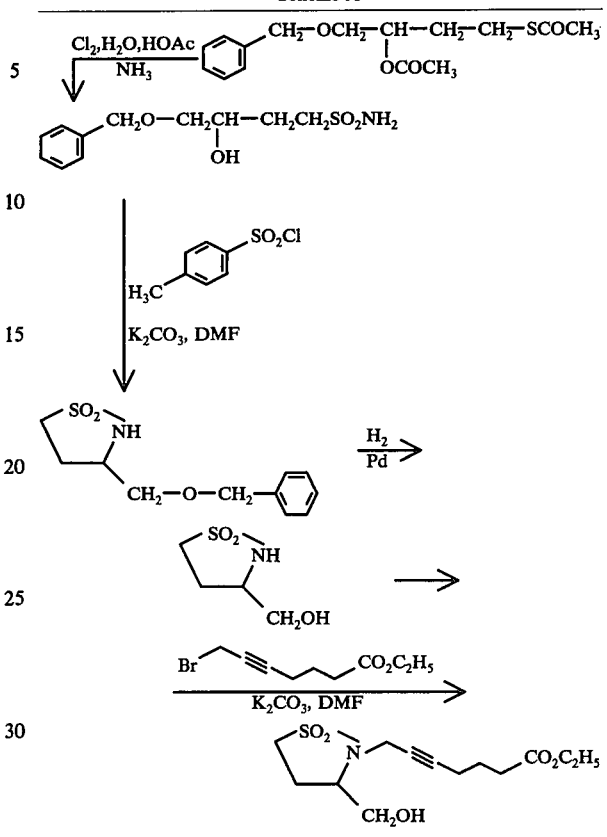

The preparation of intermediate III is seen to involve the following steps: (1) the Grignard reaction of vinylmagnesium bromide with phenoxyacetaldehyde and subsequent acetylation of the complex to yield 4-benzyloxy-3-acetoxy-1-butene; (2) the free radical addition of thiolacetic acid to the double bond of the latter product to yield S-acetyl-3-acetoxy-4-benzyloxy-1-butanethiol; (3) the oxidation of the thiol with chlorine in aqueous acetic acid and reaction of the resulting sulfonyl chloride with ammonia to yield 4-benzyloxy-3-hydroxy-1-butanesulfonamide; (4) tosylation of this compound with p-toluenesulfonyl chloride in pyridine and ring closure with potassium carbonate in dimethylformamide; (5) hydrogenolysis of the protecting benzyl group over a palladium catalyst to yield 3-(hydroxymethyl)isothiazolidine 1,1-dioxide; and (6) alkylation of the latter compound with a lower alkyl ester of 7-bromo-5-heptynoic acid, preferably ethyl 7-bromo-5-heptynoate in dimethylformamide in the presence of potassium carbonate to yield intermediate III.

To prepare the carboxylic acid of formula II wherein A is cis-vinylene and Z is trans-vinylene (II$_A$), the intermediate III is first hydrogenated over a Lindlar catalyst (a palladium catalyst partially poisoned with lead acetate) to convert the triple bond of III to a cis-olefinic bond. The hydroxymethyl group of the product is oxidized to formyl preferably with a chromic acid type oxidizing agent such as pyridinium chlorochromate. The resulting aldehyde is condensed with the ylide prepared from dimethyl (2-oxoheptyl)phosphonate to afford the α,β-unsaturated ketone. The carbonyl group of this intermediate is reduced to carbinol with sodium or potassium borohydride in solution in ethanol or diglyme at from −5° to 15° C. and the ester function hydrolyzed under basic conditions, preferably with sodium or potassium carbonate in aqueous methanol or ethanol to obtain the carboxylic acid product of formula II (II$_A$) wherein A is cis-vinylene and Z is trans-vinylene. The above process for the synthesis of compound II$_A$ is outlined in Scheme B.

Scheme B

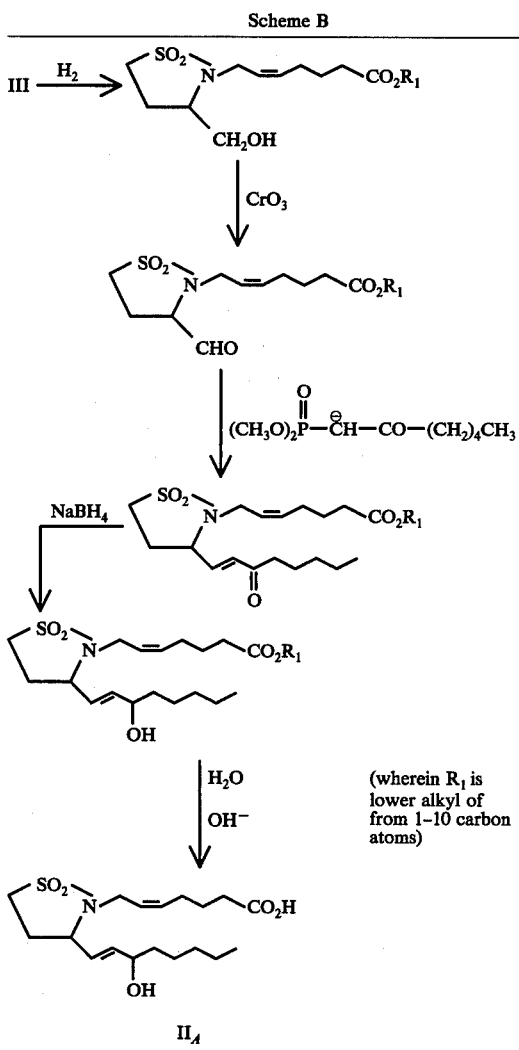

To prepare the carboxylic acid of formula II wherein A is ethylene and Z is trans-vinylene, the intermediate III is hydrogenated over either a platinum or palladium catalyst to convert the triple bond of III to a single bond with the uptake of two molar equivalents of hydrogen. The remainder of the synthesis is conducted as for compound II$_A$ including the oxidation, condensation, hydride reduction, and hydrolysis steps.

To prepare the carboxylic acid of formula II wherein A and Z are both ethylene, the product compound II$_A$ is hydrogenated preferably over a platinum or palladium catalyst in a suitable solvent such as ethanol or ethyl acetate at a temperature from 20° to 40° C. to effect the reduction of both double bonds with the uptake of two molar equivalents of hydrogen.

To obtain carboxy salts, the acid products (II) are dissolved in a solvent such as ethanol, methanol, glyme, and the like, and the solution treated with an appropriate alkali or alkaline earth hydroxide or alkoxide to yield the metal salt, or with an equivalent quantity of ammonia, amine, or quaternary ammonium hydroxide to yield the amine salt. In each instance, the salt either separates from the solution and may be separated by filtration or, when the salt is soluble, it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine, or a quaternary ammonium hydroxide.

To obtain carboxy esters (i.e., compounds of formula I where R is alkoxycarbonyl), the acid products (II) are treated in ether with an ethereal solution of the appropriate diazoalkane. For example, methyl esters are obtained by the use of diazomethane.

EXAMPLE 1

Preparation of 7-[3-(3-Hydroxy-1-trans-octenyl)-2-isothiazolidinyl]-5-cis-heptenoic Acid S,S-Dioxide Step A. Preparation of 4-Benzyloxy-3-acetoxy-1-butene Magnesium metal (5 g., 0.206 mole) is suspended in tetrahydrofuran (100 ml.) in a three-necked, round-bottomed flask protected by a dry ice condenser and equipped with a mechanical stirrer. The stirrer is started and vinyl bromide (22 g., 0.206 mole) in tetrahydrofuran is added at such a rate as to keep the solvent refluxing. The reaction mixture is refluxed for 0.5 hours after the addition is complete. The reaction mixture is then cooled to 0°–5° C. and benzyloxyacetaldehyde (24 g., 0.16 mole) in tetrahydrofuran (15 ml.) is added dropwise. After 1.5 hours at 0°–5° C., there is added acetic anhydride (26 g., 0.255 mole) and the reaction mixture is allowed to come to room temperature. After 20 hours at room temperature, ice water (500 ml.) is added and the product is extracted into ethyl acetate (3 × 100 ml.). The ethyl acetate extract is washed with brine, dried (Na$_2$SO$_4$), and distilled. There is obtained 17 g. (49%) of the title compound, b.p. 85°–95° C./0.05 mm.

Anal. Calcd. for C$_{13}$H$_{16}$O$_3$·0.5H$_2$O: C, 68.10; H, 7.47. Found: C, 67.94; H, 7.41.

Step B: Preparation of S-Acetyl-3-acetoxy-4-benzyloxy-1-butanethiol

A solution of thiolacetic acid (10.0 g., 0.13 mole) and 4-benzyloxy-3-acetoxy-1-butene (21.0 g., 0.096 mole) containing benzoxyl peroxide (50 mg.) is stirred at room temperature for 20 hours. The reaction mixture is taken up in ether (200 ml.), washed with saturated sodium bicarbonate solution until neutral and then with brine and dried over sodium sulfate. The ether is removed in vacuo and the resulting oil is purified by chromatography over silica gel using hexane-ethyl acetate (80-20) to elute. From the proper fraction there is obtained 18.0 g. (64%) of the title compound as a heavy oil.

Anal. Calcd. for C$_{15}$H$_{20}$O$_4$S: C, 60.79; H, 6.80. Found: C, 60.39; H, 6.66.

Step C. Preparation of 4-Benzyloxy-3-hydroxy-1-butanesulfonamide

A solution of S-acetyl-3-acetoxy-4-benzyloxy-1-butanethiol (9.0 g., 0.03 mole) in 80% aqueous acetic acid (80 ml.) is stirred, cooled in an ice bath, and treated with chlorine gas at such a rate as to keep the temperature below 15° C. When the solution becomes saturated with chlorine (ca. ½ hour), the addition of the gas is stopped. After 0.5 hours longer at 10°–15° C., a stream of nitrogen is bubbled through the solution until excess chlorine is removed. The reaction mixture is poured into water (500 ml.) and extracted with ether (2 × 200 ml.). The ether solution is washed with brine, dried over sodium sulfate, and then concentrated in vacuo. Benzene is used to azeotropically remove any acetic acid or water that remains on the product. The dried, heavy oil is added carefully to stirred liquid ammonia (100 ml.). The reaction mixture is allowed to stand 20 hours during which time most of the ammonia evaporates. Water (150 ml.) is added to the residue and excess base is neutralized with dilute hydrochloric acid. The crude product separates as a white solid which is recovered by filtration and dried. There is obtained 6.3 g. (80%) of the title compound, m.p. 94°–98° C. A pure sample is obtained by recrystallization from benzene, m.p. 100°–102° C.

Anal. calcd. for $C_{11}H_{17}NO_4S$: C, 50.94; H, 6.60; N, 5.40. Found: C, 50.92; H, 6.42; N, 5.11.

Step D. 3-(Benzyloxymethyl)isothiazolidine 1,1-Dioxide

To a solution of 4-benzyloxy-3-hydroxy-1-butane-sulfonamide (1.6 g., 0.0062 mole) in pyridine (15 ml.), which is stirred and cooled in an ice bath, is added p-toluenesulfonyl chloride (1.18 g., 0.0062 mole). The reaction mixture is stirred at room temperature for 20 hours and then poured into water (100 ml.). This mixture is extracted with ethyl acetate-ether (1:1) (2 × 100 ml.). The organic phase is washed with brine, 3N hydrochloric acid, brine again, and then dried over sodium sulfate. Evaporation affords an oil that is dissolved in dimethylformamide (15 ml.); potassium carbonate (1.2 g.) is added, and the mixture is heated on the steam bath for 2.5 hours. Water is added to the cooled mixture, which is acidified (dilute HCl) and then extracted with ethyl acetate (2 × 75 ml.). The organic phase is washed with brine, dried over sodium sulfate, and concentrated in vacuo. The resulting oil is purified by chromatography over silica gel using ethyl acetate-hexane (60:40) to elute. From the proper fraction, there is obtained 1.2 g. (81%) of the title compound as a clear, viscous oil.

tlc - $SiO_2$ - Ethyl acetate-hexane (60:40) $R_f$=0.55.

Anal. Calcd. for $C_{11}H_{15}NO_3S$: C, 54.75; H, 6.26; N, 5.80. Found: C, 54.70; H, 6.44; N, 5.53.

Step E. 3-(Hydroxymethyl)isothiazoidine 1,1-Dioxide

A mixture containing 3-(benzyloxymethyl)isothiazolidine 1,1-dioxide (1.2 g., 0.005 mole) and 10% palladium on carbon catalyst (300 mg.) in ethyl acetate-ethanol (1:1) (25 ml.) is hydrogenated on a Hirschberg apparatus until hydrogen uptake stops. There is absorbed 120 ml. of hydrogen (theory being 112 ml.). The reaction mixture is then filtered to remove the catalyst and concentrated in vacuo. There is obtained 750 mg. (98%) of the title compound as a pale yellow oil.

Anal. Calcd. for $C_4H_9NO_3S.0.5\ H_2O$: C, 29.99; H, 6.29; N, 8.74; S, 20.02. Found: C, 30.57; H, 6.18; N, 8.80; S, 19.97.

Step F: Preparation of Ethyl 7-(3-Hydroxymethyl-2-isothiazolidinyl)-5-heptynoate S,S-Dioxide To a mixture of potassium carbonate (2.1 g., 0.015 mole) and 3-(hydroxymethyl)isothiazolidine 1,1-dioxide (1.5 g., 0.01 mole) in dimethylformamide (15 ml.) is added ethyl 7-bromo-5-heptynoate (2.3 g., 0.01 mole) and the reaction mixture is stirred 20 hours at room temperature. The reaction mixture is poured into water (100 ml.), acidified (dilute HCl), and extracted with ethyl acetate (2 × 75 ml.). The organic phase is washed with brine, dried over sodium sulfate, and concentrated in vacuo. The resulting oil is chromatographed over silica gel using ethyl acetate-hexane (70:30) to elute. From the proper fractions, there is obtained 1.65 g. (55%) of the title compound as a heavy oil.

Anal. Calcd. for $C_{13}H_{21}NO_5S.0.5\ H_2O$: C, 49.98; H, 7.09; N, 4.48. Found: C, 49.93; H, 7.01; N, 4.30.

Step G. Preparation of Ethyl 7-(3-Hydroxymethyl-2-isothiazolidinyl)-5-cis-heptenoate S,S-Dioxide A mixture of Lindlar catalyst (200 mg.) and ethyl 7-(3-hydroxymethyl-2-isothiazolidinyl)-5-heptynoate S,S-dioxide (1.7 g., 0.0056 mole) in ethyl acetate (25 ml.) is hydrogenated on a Hirschberg apparatus until hydrogen uptake stops. There is absorbed 130 ml. of hydrogen (theory is 127 ml.). The reaction mixture is filtered and then concentrated in vacuo. There is obtained 1.6 g. (94%) of the title compound as a heavy oil.

Anal. Calcd. for $C_{13}H_{23}NO_5S$: C, 51.13; H, 7.59; N, 4.59. Found: C, 50.96; H, 7.77; N, 4.71.

Step H. Preparation of Ethyl 7-(3-Formyl-2-isothiazolidinyl)-5-cis-heptenoate S,S-Dioxide A solution of ethyl 7-(3-hydroxymethyl-2-isothiazolidinyl)-5-cis-heptenoate S,S-dioxide (1.8 g., 0.0059 mole) in methylene chloride (50 ml.) is stirred at room temperature and pyridinium chlorochromate (2.1 g., 0.01 mole) is added in one portion. After 2 hours, an additional 0.5 g. of the pyridinium chlorochromate is added. At the end of 5 hours, the reaction is judged to be complete by tlc and a solution of ethyl acetate-ether (1:1) (100 ml.) is added. The organic phase is decanted and the black residue is washed with several portions of ethyl acetate-ether (1:1). The combined organic extracts are washed with dilute sodium bicarbonate, brine and then dried over sodium sulfate. The solvent is removed in vacuo, leaving 1.7 g. (95%) of the crude title compound, which is not purified further.

Step I. Preparation of Ethyl 7-[3-(3-oxo-1-trans-octenyl)-2-isothiazolidinyl]-5-cis-heptenoate S,S-Dioxide Sodium hydride (142 mg., 0.0059 mole) is suspended in dry dimethoxyethane (50 ml.) which is cooled in an ice bath and stirred magnetically, and dimethyl (2-oxoheptyl)phosphonate (1.34 g., 0.0059 mole) is added dropwise. After one hour, a solution of ethyl 7-(3-formyl-2-isothiazolidinyl)-5-cis-heptenoate S,S-dioxide (1.8 g., 0.0059 mole) in dimethoxyethane (5 ml.) is added, and the reaction mixture is allowed to warm to room temperature over 2.5 hours. Brief warming (50° C.) affords a clear solution. The cooled reaction mixture is added to water and extracted with ether (3 × 100 ml.). The organic phase is washed with brine and dried over sodium sulfate. Evaporation of the solvent affords an oil which is chromatographed over silica gel using ethyl acetatehexane (80:20) to elute. There is obtained 300 mg. (13%) of the title compound as an oil which is used in the next reaction.

Step J. Preparation of 7-[3-(3-Hydroxy-1-trans-octenyl)-2-isothiazolidinyl]-5-cis-heptenoic Acid S,S-Dioxide An ethanol (10 ml.) solution of ethyl 7-[3-(3-oxo-1-trans-octenyl)-2-isothiazolidinyl]-5-cis-heptenoate S,S-dioxide (300 mg., 0.00075 mole) is stirred and cooled in an ice bath and sodium borohydride (30 mg., excess) is added. After one hour, water (50 ml.) is added and the mixture is extracted with ethyl acetate (2 × 50 ml.). The organic phase is washed with brine, dried over sodium sulfate, and concentrated in vacuo. The residue is dissolved in methanol (5 ml.), water (0.2 ml.) and solid potassium carbonate (200 mg.) is added. This mixture is stirred 20 hours at room temperature and then water (50 ml.) is added. The aqueous solution is acidified (dilute HCl) and extracted with ethyl acetate (2 × 25 ml.). The organic phase is washed with brine, dried over sodium sulfate, and concentrated in vacuo. The resulting oil is chromatographed over silica gel using chloroform-methanol (85:15) to elute. There is obtained 100 mg. (37%) of the title compound as a heavy oil.

Anal. Calcd. for $C_{18}H_{31}NO_5S$: C, 57.88; H, 8.36; N, 3.75. Found: C, 57.44; H, 8.43; N, 3.68.

EXAMPLE 2

Preparation of 7-[3-(3-Hydroxy-1-trans-octenyl)-2-isothiazolidinyl]-heptanoic Acid S,S-Dioxide

Step A. Preparation of Ethyl 7-(3-Hydroxymethyl-2-isothiazolidinyl)heptanoate S,S-Dioxide Ethyl 7-(3-hydroxymethyl-2-isothiazolidinyl)-5-heptynoate S,S-dioxide (2.5 g., 0.008 mole) (Example 1, Step F) dissolved in ethanol (40 ml. is hydrogenated at 1 atmosphere pressure and 27° C. over a 10% palladium on charcoal catalyst (250 mg.). When the required 0.016 mole of hydrogen is absorbed, the catalyst is removed by filtration and the solvent ethanol distilled at reduced pressure to afford the title compound as a viscous residual oil.

Step B. Preparation of 7-[3-(3-Hydroxy-1-trans-octenyl)-2-isothiazolidinyl]-heptanoic Acid S,S-Dioxide This compound is prepared by following the procedures described in Example 1, Steps H through J, but substituting in Step H an equivalent quantity of ethyl 7-(3-hydroxymethyl-2-isothiazolidinyl)heptanoate S,S-dioxide for ethyl 7-(3-hydroxymethyl-2-isothiazolidinyl)-5-cis-heptenoate S,S-dioxide. There are thus obtained in succession: ethyl 7-(3-formyl-2-isothiazolidinyl)-heptanoate S,S-dioxide (Step H); ethyl 7-[3-(3-oxo-1-trans-octenyl)-2-isothiazolidinyl]heptanoate S,S-dioxide (Step I); and 7-[3-(3-hydroxy-1-trans-octenyl)-2-isothiazolidinyl]heptanoic acid S,S-dioxide (Step J).

EXAMPLE 3

Preparation of 7-[3-(3-Hydroxyoctyl)-2-isothiazolidinyl]-heptanoic Acid S,S-Dioxide A solution of 7-[3-(3-hydroxy-1-trans-octenyl)-2-isothiazolidinyl]-5-cis-heptenoic acid S,S-dioxide (1.1 g., 0.003 mole) in ethanol (20 ml.) in which is suspended a 10% palladium on carbon catalyst (150 mg.) is hydrogenated at 1 atmosphere pressure and 27° C. The uptake of hydrogen ceases when approximately 0.006 mole has been absorbed. The catalyst is removed by filtration and the solvent is evaporated at reduced pressure to afford the title compound as a nearly colorless, viscous oil.

EXAMPLE 4

Preparation of Methyl 7-[3-(3-Hydroxy-1-trans-octenyl)-2-isothiazolidinyl]-5-cis-heptenoate S,S-Dioxide A solution of diazomethane (approximately 0.25 g., 0.006 mole) in ether (10 ml.) is mixed with a solution of 7-[3-(3-hydroxy-1-trans-octenyl)-2-isothiazolidinyl]-5-cis-heptenoic acid S,S-dioxide (1.112 g., 0.003 mole) in ether (5 ml.). The resulting solution is allowed to stand 4 hours at room temperature. Acetic acid is then added to destroy the excess diazomethane and the solution is washed with dilute sodium bicarbonate solution and water and dried over sodium sulfate. Evaporation of volatile materials at reduced pressure yields tht title ester as a slightly yellowish, viscous oil.

What is claimed is:

1. The compound having the following formula:

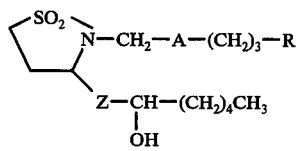

wherein
R is carboxy, a carboxy salt wherein R is $COO^\ominus M^\oplus$ wherein M is a pharmaceutically acceptable cation derived from a metal or an amine, or alkoxycarbonyl having the formula $COOR^1$ wherein $R^1$ is alkyl having 1–10 carbon atoms;
A is ethylene and cis-vinylene; and
Z is ethylene and trans-vinylene.

2. The compound of claim 1 wherein R is alkoxycarbonyl —$COOR^1$ wherein $R^1$ is alkyl having 1–10 carbon atoms.

3. Methyl 7-[3-(3-Hydroxy-1-trans-octenyl)-2-isothiazolidinyl]-5-cis-heptenoate S,S-dioxide, the compound of claim 2 wherein $R^1$ is methyl; A is cis-vinylene; and Z is trans-vinylene.

4. The compound of claim 1 which has the formula:

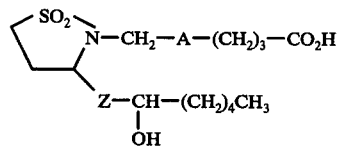

wherein A is ethylene and cis-vinylene; and Z is ethylene and trans-vinylene.

5. 7-[3-(3-Hydroxy-1-trans-octenyl)-2-isothiazolidinyl]-5-cis-heptenoic acid S,S-dioxide, the compound of claim 4 wherein A is cis-vinylene and Z is trans-vinylene.

6. 7-[3-(3-Hydroxy-1-trans-octenyl)-2-isothiazolidinyl]heptanoic acid S,S-dioxide, the compound of claim 4 wherein A is ethylene and Z is cis-vinylene.

7. 7-[3-(3-Hydroxyoctyl)-2-isothiazolidinyl]-heptanoic acid S,S-dioxide, the compound of claim 4 wherein A and Z are both ethylene.

* * * * *